United States Patent [19]

Takeuchi

[11] Patent Number: 4,738,824

[45] Date of Patent: Apr. 19, 1988

[54] APPARATUS FOR DYEING SPECIMENS AUTOMATICALLY PREPARATORY TO MICROSCOPIC EXAMINATION

[75] Inventor: Toshiyasu Takeuchi, Togura, Japan

[73] Assignees: Kabushiki Kaisha Tiyoda Seisakusho, Koushoku; Sakura Seiki Kabushik Kaisha, Tokyo, both of Japan

[21] Appl. No.: 919,184

[22] Filed: Oct. 15, 1986

[51] Int. Cl.[4] .................... G01N 35/04; G01N 37/00; B05C 3/02; B01L 11/00
[52] U.S. Cl. ........................ 422/63; 118/425; 422/65; 422/104; 427/2; 427/4; 436/46
[58] Field of Search .................. 118/425; 427/2, 4; 422/63, 65, 73, 104, 67; 436/46

[56] References Cited

U.S. PATENT DOCUMENTS

| | | | |
|---|---|---|---|
| 3,604,436 | 9/1971 | Lipshaw | 118/425 |
| 3,674,040 | 7/1972 | Howells et al. | 118/425 |
| 3,837,795 | 9/1974 | Becker et al. | 118/425 |
| 4,267,149 | 5/1981 | Bruckner et al. | 422/65 |
| 4,451,433 | 5/1984 | Yamashita et al. | 422/63 |

OTHER PUBLICATIONS

Fisher 86–Slide Staine–Apr. 23, 1985.

*Primary Examiner*—Michael S. Marcus
*Attorney, Agent, or Firm*—Ladas & Parry

[57] ABSTRACT

An automatic dyeing apparatus has a casing, a plurality of vessels arranged in the casing, a specimen cage transporting mechanism and a controller capable of moving each cage with a plurality of pieces of slide glass to a predetermined position whereby various dyeing operations can be carried out at the same time.

8 Claims, 7 Drawing Sheets

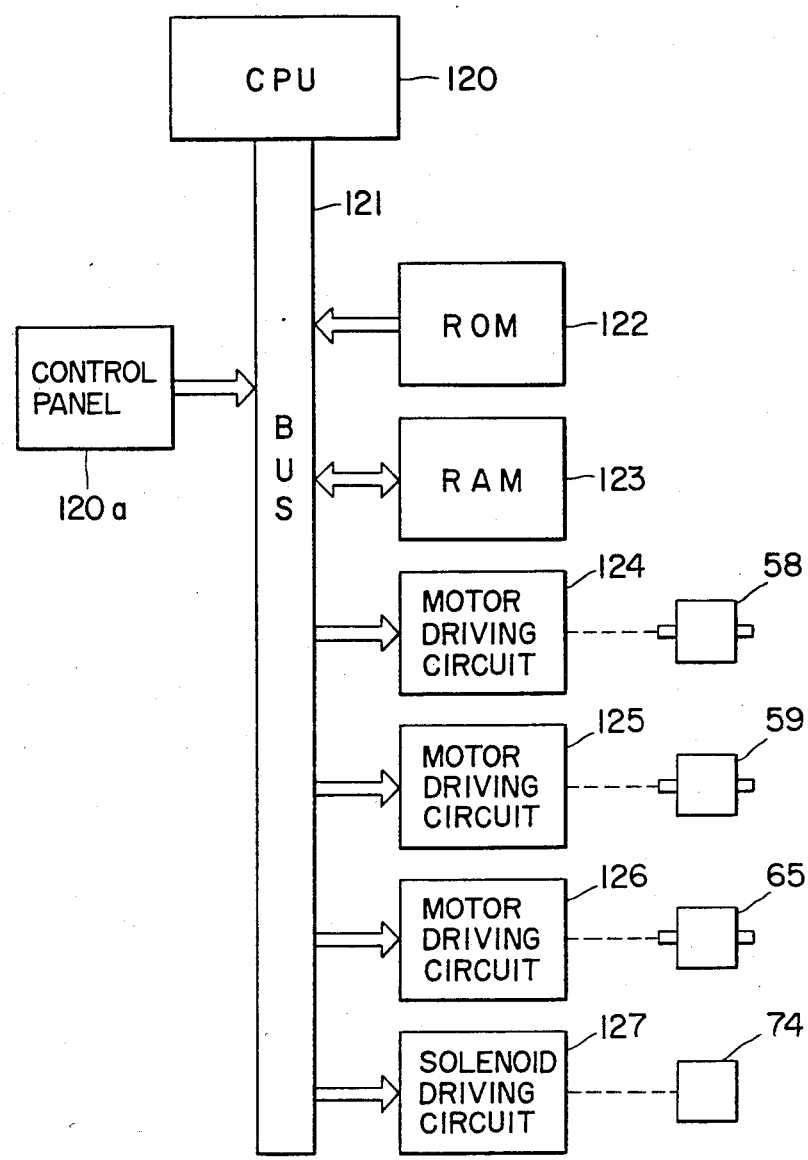
F I G. 15

APPARATUS FOR DYEING SPECIMENS AUTOMATICALLY PREPARATORY TO MICROSCOPIC EXAMINATION

BACKGROUND OF THE INVENTION

This invention relates to an apparatus for dyeing automatically specimens such as pieces of tissue or cell attached to a piece of slide glass preparatory to microscopic examination.

In a hospital or laboratory, specimens taken out of an affected part of a patient are often examined by a microscope to find a cause of his disease. In order to facilitate microscopic examination, the specimens attached to a piece of slide glass are usually dyed. There have appeared a variety of apparatuses for carrying out automatically a dyeing operation.

In these conventional apparatuses, a plurality of vessels each containing a kind of reagent are placed on a table and each slide glass with a specimen is immersed in each vessel in a prescribed order.

As dyeing methods, HE method, MASSON method, etc. are well known. A suitable dyeing method must be selected depending on kind of specimens or cells to be investigated.

However, each conventional apparatus can carry out only one specific dyeing method and cannot carry out a plurality of dyeing methods by itself because different reagents and structures are required depending on kind of dyeing methods. Accordingly, in order to dye many kinds of specimens, a plurality of dyeing apparatus must be prepared thereby to require much cost and a wide space.

SUMMARY OF THE INVENTION

It is an object of this invention to provide an apparatus for dyeing specimens automatically in preparation for microscopic investigation which can carry out efficiently a plurality of dyeing methods at the same time.

According to this invention, there is provided an apparatus for dyeing specimens automatically preparatory to microscopic examination, which comprises: a casing; a plurality of vessels containing various reagents and arranged regularly in the casing; a specimen cage transporting mechanism for transporting each cage accommodating at least one slide glass with a specimen from one vessel to other vessels, said mechanism having a support head for holding each cage and releasing it in each vessel, the support head being moved in the longitudinal, lateral and vertical directions of the casing; and a controller for controlling the movement of the specimen cage transporting mechanism.

The nature, utility, and further features of this invention will be more clearly apparent from the following detailed description with respect to preferred embodiments of the invention when read in conjunction with the accompanying drawings briefly described below.

BRIEF DESCRIPTION OF THE DRAWINGS

In the accompanying drawings:

FIG. 15 is a block diagram of a controller.

DETAILED DESCRIPTION OF THE INVENTION

Figure 1:
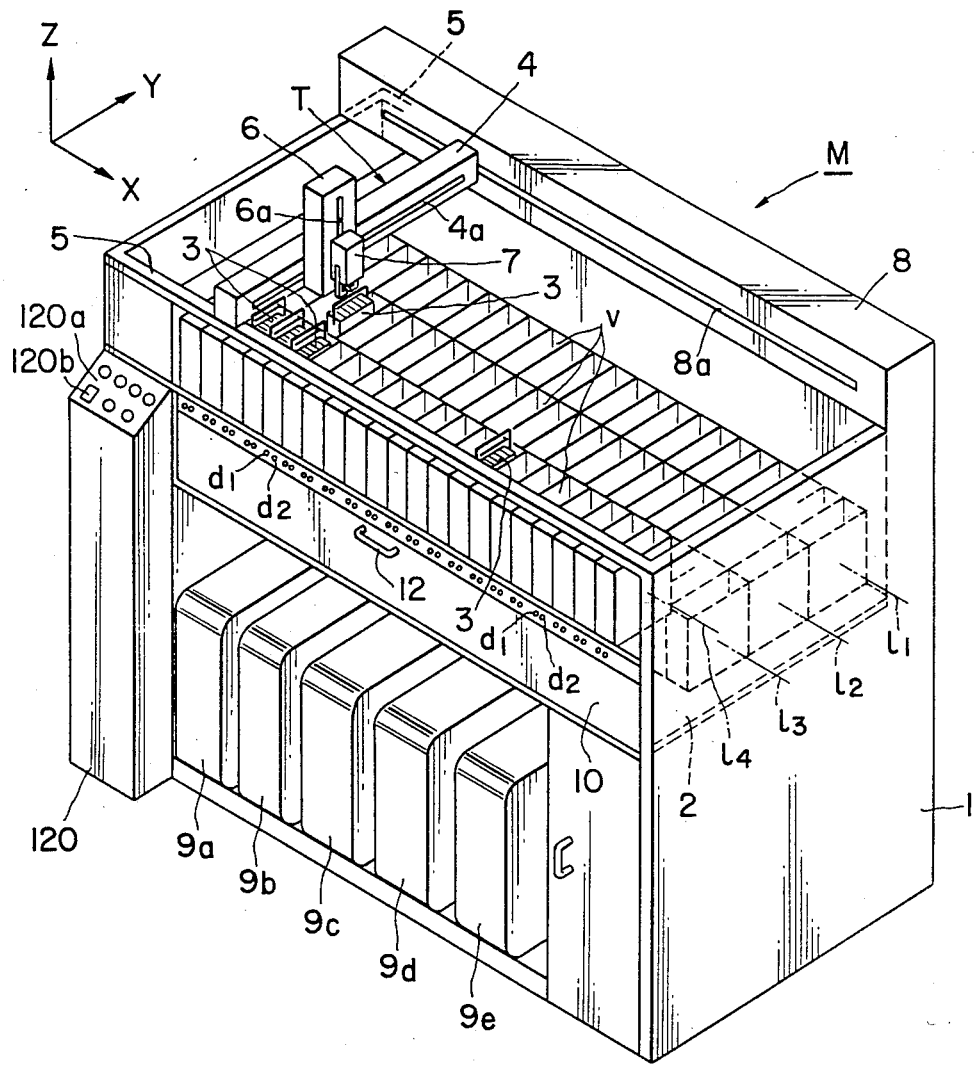
FIG. 1 is a perspective view of an automatic dyeing apparatus according to this invention.
Figure 2:
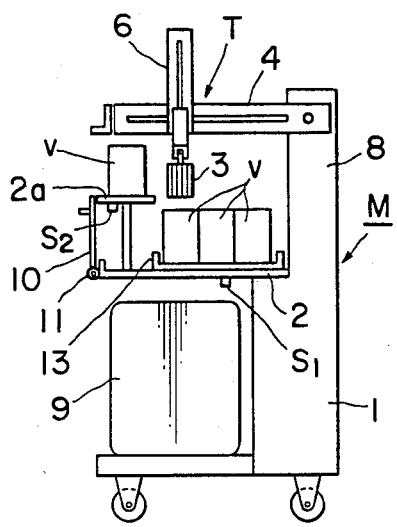
FIG. 2 is a side view of the apparatus.

Referring to FIGS. 1 and 2, an automatic dyeing apparatus M for dyeing specimens such as tissue or cell has a casing 1, in the upper portion of which a horizontal main table 2 is provided for disposing regularly many vessels v, v, . . . v thereon, each containing a kind of liquid such as reagent and water for dyeing specimens. Each vessel v has an open top face through which a specimen cage 3 for supporting many pieces of slide glass with specimens is immersed into the reagent or water of each vessel v. On the upper face of the casing 1 is provided a specimen cage transporting mechanism T for transporting specimen cages into the respective vessels v. The mechanism T has a first slide body 4 extending laterally over the vessels v arranged on the main table 2 and the first slide body 4 is moved in the longitudinal direction (X direction) of the casing 1 while its opposite ends slide on respective guide rails 5, 5. Further, the first slide body 4 has a second slide body 6 extending vertically which is moved along the first slide body 4 in the lateral direction (Y direction) of the casing 1. The second slide body 6 has a support head 7 for supporting a specimen cage and the support head 7 is moved vertically along the second slide body 6 in the vertical direction (Z direction). The two slide bodies 4, 6 have two slits $4a$, $6a$ formed on one side wall of their respective casings and one end of the first slide body 4 is moved along a slit $8a$ provided in an upper casing 8 which is formed on the back side of the upper portion of the casing 1. The casing 1 accommodates a plurality of reagent tanks $9a$, $9b$, . . . , $9e$ at its bottom.

Figure 3:
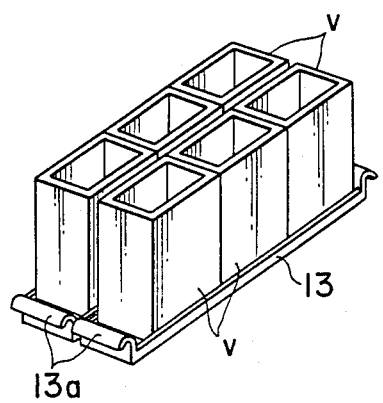
FIG. 3 is a perspective view of vessels placed on trays.

On the horizontal main table 2 are arranged a great many vessels v so as to form three lines $l_1$, $l_2$, $l_3$. On the front side of the main table 2 is provided an upper table $2a$ which is located in a position upper than that of each vessel v on the table 2 and which supports a line of vessels v accommodating xylene as a reagent. The vessels v form one line $l_4$ on the upper table $2a$ and the space between the upper table $2a$ and the main table 2 is closed by a cover 10 with a handle 12, which is swingable about a hinge 11. Each vessel v for a dyeing reagent on the main table 2 is placed on each tray 13 as shown in FIG. 3. That is, three vessels v are set on one tray 13 adjacent to each other in its longitudinal direction. Each tray 13 has a handle portion $13a$ at its front end and an operator sets each vessel v on the main table 2 and takes them out therefrom by sliding each tray 13 on the main table 2 through the space between the two tables 2, $2a$ in a state wherein the cover 10 is opened.

Figure 4:
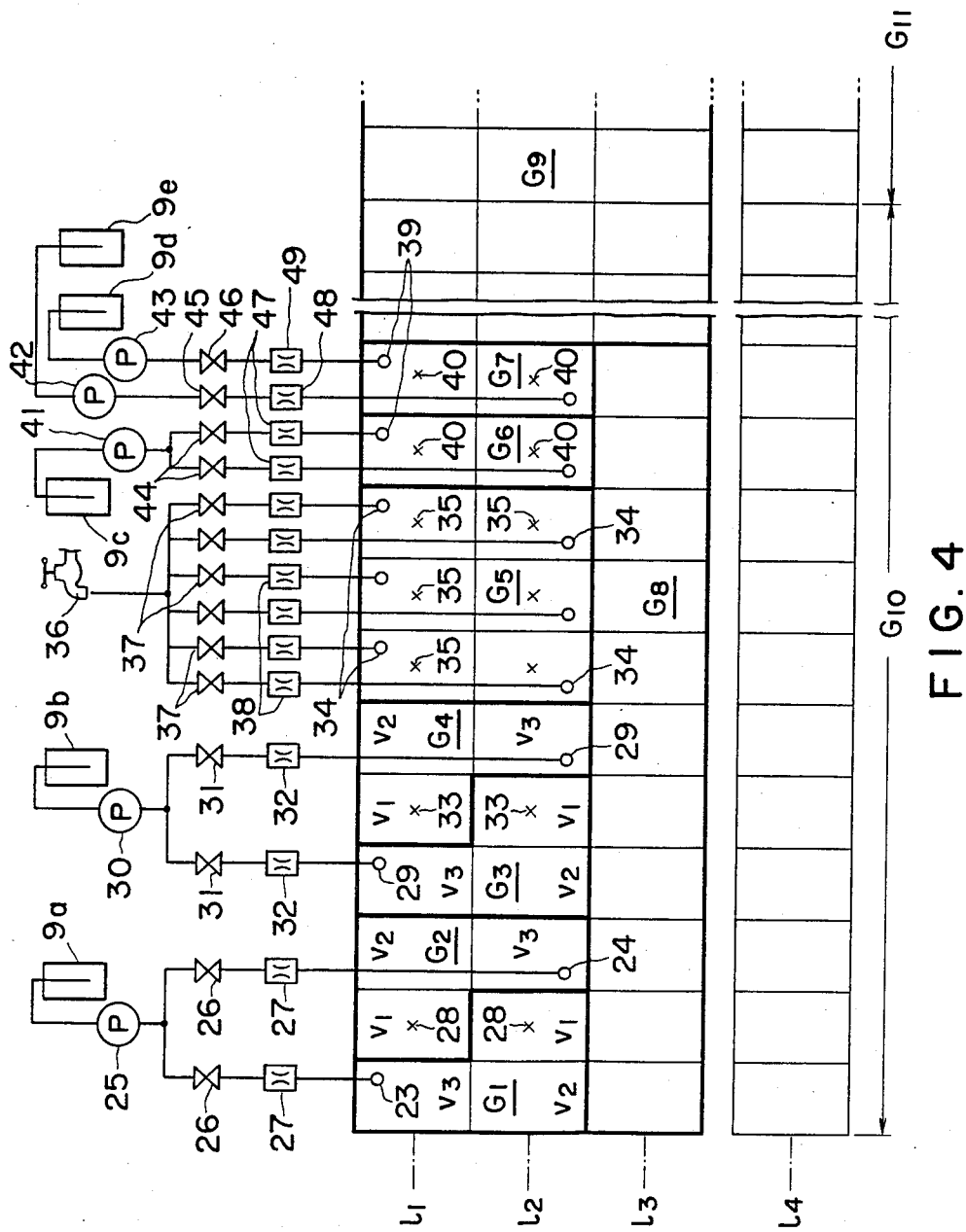
FIG. 4 is a view showing disposition of vessels.

The disposition of the above vessels v will now be explained with reference to FIG. 4.

On the left side of the main table 2 are placed a plurality of vessels directly without trays and the vessels are divided into several groups $G_1, G_2, \ldots, G_8$. The groups $G_1, G_2$ comprise three vessels $v_1, v_2, v_3$ for xylene, respectively, the groups $G_3, G_4$ comprise three vessels $v_1, v_2, v_3$ for alcohol, the group $G_5$ comprises six vessels for water, the group $G_6$ comprises two vessels for distilled water, the group $G_7$ comprises two supplementary vessels and the gorup $G_8$ comprises many preliminary vessels in the line $l_3$. The great many vessels placed on the trays 13 and located on the right side of the above groups $G_1, G_2, \ldots, G_8$ form a group $G_9$ for accommodating various reagents for dyeing specimens in the cage 3.

Figure 5:
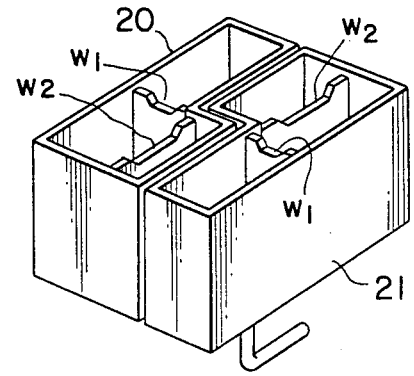
FIG. 5 is a perspective view of assembled vessels.

The groups $G_1, G_2, \ldots, G_4$ have special vessels as shown in FIG. 5, respectively. That is, the group $G_1$ comprises an assembled container 20 in the shape of a letter L as viewed in a plan view and the group $G_2$ comprises also an assembled container 21 having a shape complementary to the container 20. The groups $G_1, G_2$ have three vessels $v_1, v_2, v_3$ partitioned by two partition walls $w_1, w_2$, respectively. In both groups $G_1, G_2$, the vessels $v_3, v_3$ have two inlets 23, 24, respectively, through which xylene in a tank 9a is supplied into the respective vessels $v_3, v_3$ via a pump 25, two valves 26, 26 and two nozzles 27, 27 for adjusting flow rate of xylene. The vessels $v_1, v_1$ have two outlets 28, 28 for discharging used xylene and xylene supplied into the vessels $v_3, v_3$ flows over the partition wall $w_2, w_2$ into the adjacent vessels $v_2, v_2$ and then flows over the partition wall $w_1, w_1$ into the vessels $v_3, v_3$ with the outlets 28, 28. Accordingly, xylene in the vessels $v_3, v_3$ is always remained clean.

The groups $G_3, G_4$ have the same structure as that of the groups $G_1, G_2$. In both groups $G_3, G_4$, the vessels $v_3, v_3$ have two inlets 29, 29 through which alcohol in a tank 9b is supplied thereinto through a pump 31, two valves 31, 31 and two flow rate adjusting nozzles 32, 32, respectively. Each vessel $v_1$ has an outlet 33.

Each vessel of the group $G_5$ has an inlet 34 and an outlet 35 and water in a water source 36 is supplied into each vessel through a valve 37 and a flow rate adjusting nozzle 38. Further, each vessel of the groups $G_6, G_7$ has also an inlet 39 and an outlet 40 and respective liquids in three tanks 9c, 9d, 9e are supplied into the respective vessels through three pumps 41, 42, 43, four valves 44, 44, 45, 46 and four flow rate adjusting nozzles 47, 47, 48, 49.

Approximately half of vessels in the line $l_4$ on the upper table 2a form a group $G_{10}$ while the remaining vessels in the line $l_4$ form a group $G_{11}$. Each vessel of the groups $G_{10}, G_{11}$ contains xylene. The gourp $G_{10}$ is for accommodating each cage having some pieces of slide glass with specimens which have not been dyed yet while the group $G_{11}$ is for accommodating each cage having specimens which have already been dyed.

The construction of the specimen cage transporting mechanism T will now be explained with reference to FIGS. 6 to 9.

Figure 6:
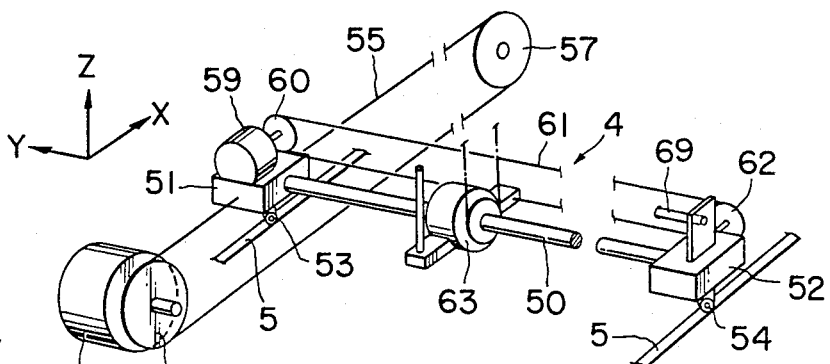
FIG. 6 is a diagrammatic view of a specimen cage transporting mechanism.
Figure 7:
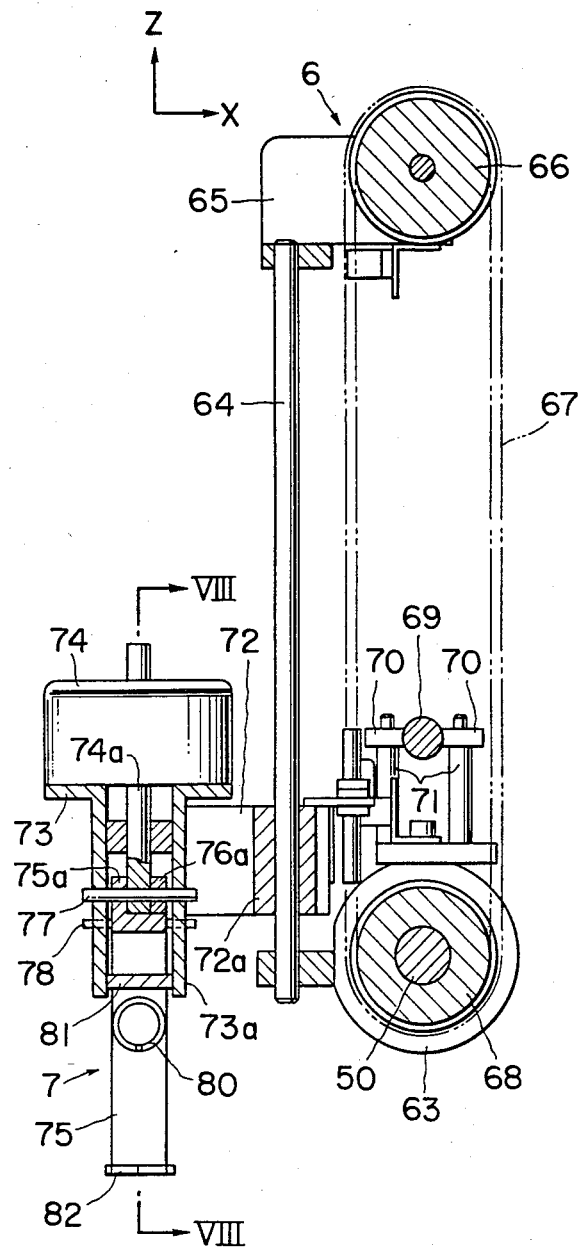
FIG. 7 is a vertically sectional view of a second slide body.

In FIGS. 6 and 7, a slide bar 50 is extended laterally (Y direction) in the first slide body 4 of the mechanism T and has two stands 51, 52 at its opposite ends. The two stands 51, 52 have two rollers 53, 54 rolling on the guide rails 5, 5, respectively. The stand 51 is connected to a wire 55 which runs reciprocally between a driving pulley 56 and a driven pulley 57 and the driving pulley 56 is driven by a pulse motor 58. On the stand 51 is supported a pulse motor 59 with a driving pulley 60 for driving a wire 61 running reciprocally between the driving pulley 60 and a driven pulley 62 provided on the opposite stand 52. To the wire 61 is connected a slide member 63 which slides on the slide bar 50. The slide member 63 has a vertical support column 64 on the top end of which a pulse motor 65 is supported. The pulse motor 65 has a driving pulley 66 for driving a wire 67 which runs reciprocally between the driving pulley 66 and a driven pulley 68 provided rotatably on the slide bar 50. Over the slide bar 50 is extended a guide bar 69, parallel to the slide bar 50, against which two guide rollers 70, 70 abut on the opposite sides of the guide bar 69. The guide rollers 70, 70 are supported on the tops of the rods 71, 71 which are fixed to the slide member 63. The wire 67 holds a support plate 72 for supporting the support head 7 and the support plate 72 has an engaging portion 72a for engaging the support plate 72 with the support column 64 which also functions as a guide column.

Figure 9:
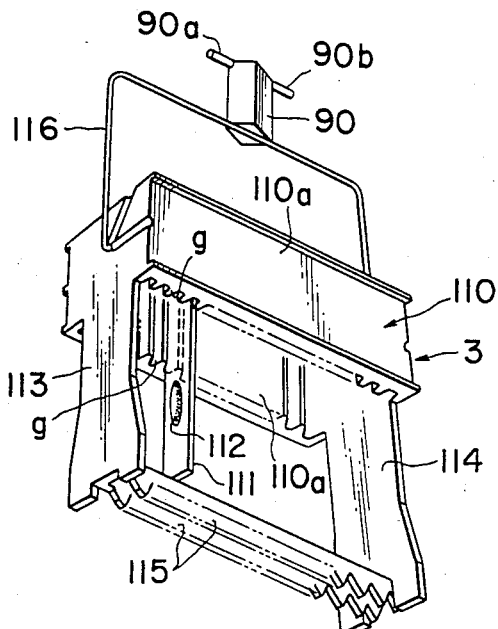
FIG. 9 is a perspective view of a cage.
Figure 10:
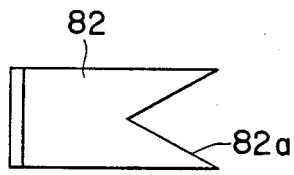
FIG. 10 is a plan view of a holding plate.
Figure 11:
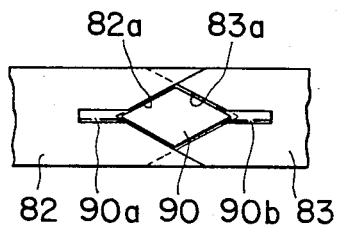
FIG. 11 is a plan view showing a state wherein two holding plates hold a suspending bar.

The head 7 has a frame 73 on which a solenoid 74 is placed and the frame 73 has two skirt portions 73a, 73a extending vertically at a predetermined space in the X direction. The skirt portions 73a, 73a support swingably two fingers 75, 76 having an L-shape and cooperating with each other to hold a specimen cage 3 as shown in FIG. 9. The solenoid 74 has an axis 74a, the lower end of which is connected to two ears 75a, 76a of the fingers 75, 76 by a pin 77. The two fingers 75, 76 are swingably supported by two pins 78, 79 at their bending portions, respectively. Further, the two fingers 75, 76 are urged toward each other by a coil spring 80 and the inward movement of the two fingers 75, 76 is restricted by a limit plate 81. The two fingers 75, 76 have two holding plates 82, 83, respectively, which has a shape as shown in FIG. 10. The holding plates 82, 83 have two triangular recesses 82a, 83a (FIG. 11), respectively, opposite to each other. The shape of each recess corresponds to that of a suspending bar 90 of the specimen cage 3 and the suspending bar 90 has two hanging bars 90a, 90b extending horizontally and laterally from the opposite side walls of the suspending bar 90. The suspending bar 90 has a diamond shape as seen vertically. The two holding plates 82, 83 are moved toward each other by the spring 80 to hold the suspending bar 90 therebetween in a state wherein the two hanging bars 90a, 90b are hung on the respective holding plates 82, 83 as shown in FIG. 11 when the solenoid 74 is de-energized. Contrary to this, when the solenoid 74 is energized, the axis 74a thereof is moved downward to swing the two fingers 75, 76 about the two pins 78, 79 and the two fingers 75, 76 are then opened to release the suspending bar 90.

Figure 8:
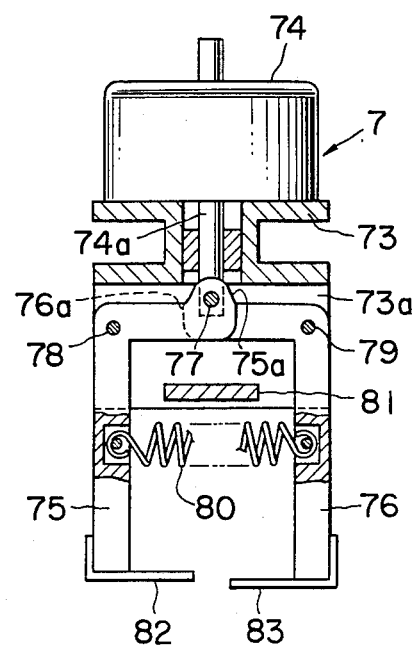
FIG. 8 is a vertically sectional view of a support head.
Figure 12:
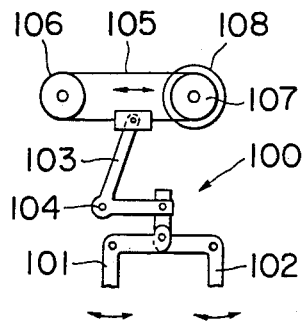
FIG. 12 is a diagrammatic view of another finger driving mechanism.

A mechanism for holding a cage 3 is not limited to that of FIGS. 7 and 8. Instead of that, a cage holding mechanism 100 as shown in FIG. 12 may be used. That is, two fingers 101, 102 are connected to one end of an L-shape lever 103 which is pivoted about a pin 104 and the other end of the L-shape lever 13 is held by a wire 105 running between two pulleys 106, 107 driven by a pulse motor 108. According to this mechanism, the swing motion of the two fingers 101, 102 can be carried out smoothly or slowly.

The specimen cage 3 has a shape shown in FIG. 9 and a head portion 110 in the shape of rectangle. The head portion 110 has two side walls 110a, 110a with a plurality of grooves at their inner surfaces, in which each piece of slide glass 111 with a specimen 112 is held vertically. The cage 3 has also two end plates 113, 114 extending vertically which support two bottom plates 115, 115 at their respective tail ends for holding each slide glass 111. On the head portion of the end plates 113, 114 is supported a hanging wire 116, the center portion of which is fixed to the lower end of the suspending bar 90.

On one side of the front face of the apparatus is provided a control box 120 having a control panel 120a for controlling the movement of the specimen cage transporting mechanism T and inputting a process program into a controller. The controller has a CPU 120, BUS 121, ROM 122 and RAM 123 and the three motors 58, 59, 65 are driven through three corresponding motor driving circuits 124, 125, 126 which are connected to the BUS 121, respectively. Further, the solenoid 74 is driven through a solenoid driving circuit 127. In FIG. 2, the main table 2 and an upper table 2a have a plurality of proximity switches $s_1, s_1, \ldots s_1, s_2, s_2, \ldots s_2$ for sensing the existence of the trays 13 and each vessel v of the line $l_4$. The proximity switches $s_1, s_2$ are provided on the back sides of the main and upper tables 2, 2a opposite to each tray 13 and each vessel of the line $l_4$, respectively. The proximity switches $s_1, s_2$ are connected to lamps $d_1, d_2$ on the front face of the casing 1, respectively.

The operation of this apparatus is carried out in the following manner.

First, five processes common to various dyeing methods will now be explained. That is, each dyeing method has paraffin removal process, first washing process, dyeing process, second washing process and dehydration and alcohol removal process. The paraffin removal process is for removing paraffin from a slice of specimen embedded in paraffin and attached to a piece of slide glass. In this paraffin removal process, xylene is used for removing paraffin and alcohol is used in preparation for the next washing process. The washing process is for removing xylene and alcohol attached to the specimen in the paraffin removal process therefrom and requires normal water and distilled water. The dyeing process is for dyeing the specimen attached to the slide glass by immersing it into a dyeing reagent corresponding to a kind of dyeing method to be carried out.

In this process, in case that a plurality of dyeing reagents are used, a washing process must be carried out between the immersions of a dyeing reagent and a next dyeing reagent. After the specimen is dyed in the dyeing reagent, the specimen is washed by the normal water and/or the distilled water. The dehydration and alcohol removal process is for removing water and alcohol attached to the specimen during the former processes in order to facilitate adhesion of oily adherent onto the slide glass and a cover glass with which the speciment on the slide glass is covered. This process requires alcohol and xylene.

In all dyeing methods, process liquids such as xylene, alcohol and normal and distilled waters are normally used and one or more dyeing reagents used for a certain dyeing method are different from those of other dyeing methods. Accordingly, the groups $G_1$ to $G_6$ in FIG. 4 are commonly used for various dyeing methods and the vessels of the group $G_9$ contain various dyeing reagents for carrying out different dyeing methods at the same time, respectively.

Figure 14:
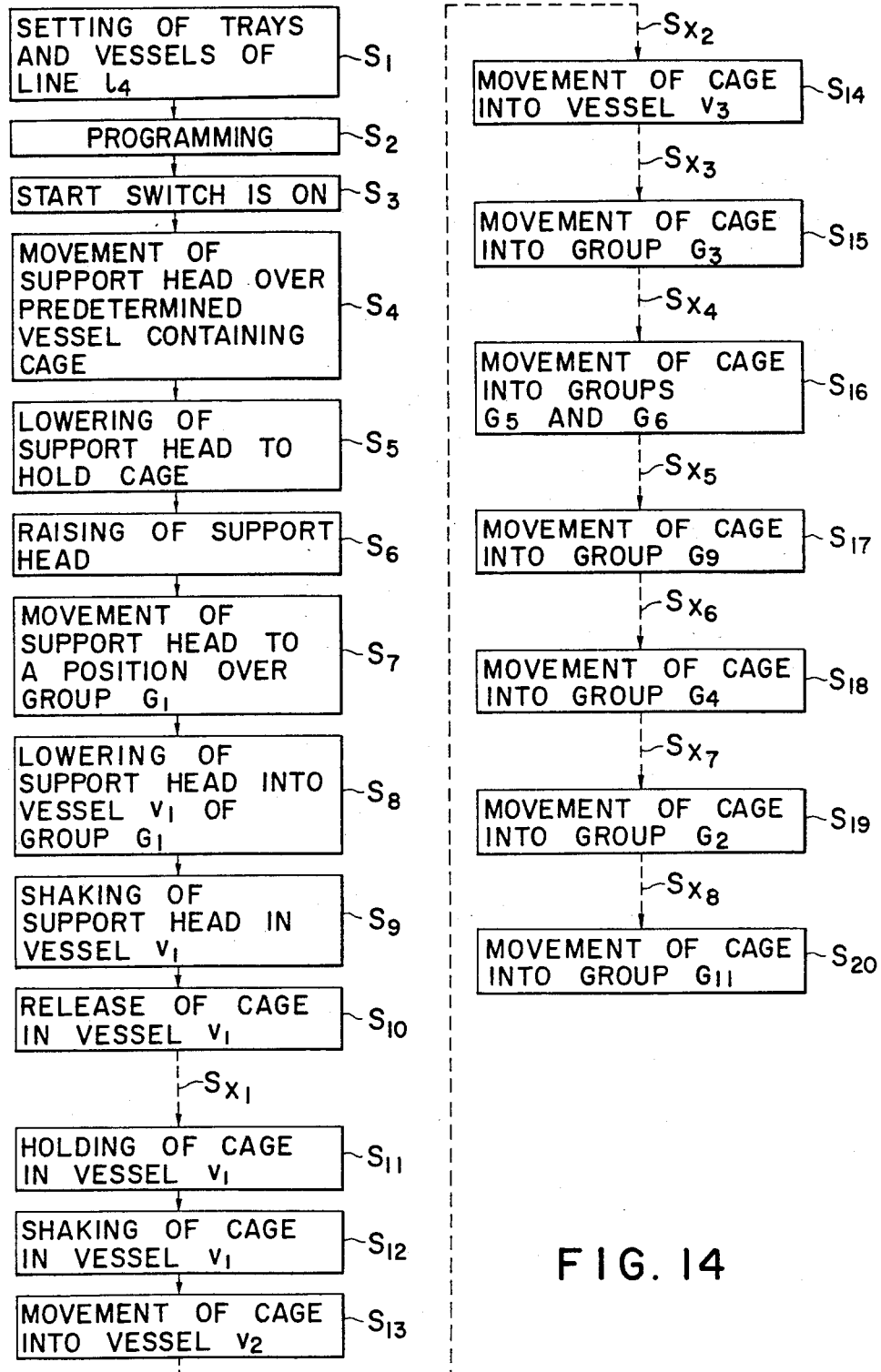
FIG. 14 is a flow chart showing a dyeing operation.

Before start of a dyeing operation, each tray 13 is taken out from the upper face of the casing 1 to fill the vessels with necessary dyeing reagents and each tray 13 with three vessels thereon is set thereinto. In addition, xylene is supplied into each vessel of the line $l_4$ on the upper table 2a (step $S_1$ in FIG. 14). If each tray 13 and the vessels of line $l_4$ are set at predetermined positions, the corresponding display lamps $d_1, d_2$ emit light. Then, a dyeing program is input into a computer of the control box 120. That is, the address of each vessel (setting position) of the group $G_{10}$ of the line $l_4$ and the dyeing program corresponding to a cage 3 of a vessel are input thereinto. In case that various dyeing programs are carried out at the same time, there may be a case that some cages 3 must be immersed into the same cages at the same time. At this time, the dyeing programs are made in a manner that some preliminary vessels are used for making some cages wait in the preliminary vessels (step $S_2$). After this, a start switch 120b on the control panel 120a is pushed (step $S_3$).

In response to the pushing of the start switch 120b, the support head 7 is moved toward a position over a certain vessel v of the group $G_{10}$ by sliding the first and second slide bodies 4, 6 while driving the pulse motors 58, 59 in response to the input program (step $S_4$). After the support head 7 reaches a position over the vessel v, the support head 7 is lowered by driving the pulse motor 65 in a state wherein the solenoid 74 is energized until the suspending bar 90 passes through the space between the two opposite holding plates 82, 83 of the fingers 75, 76 into the interior space of the two fingers 75, 76. Then, the solenoid 74 is de-energized to close the two fingers 75, 76 whereby the holding plates 82, 83 hold the suspending bar 90 therebetween (step $S_5$). Thereafter, the support head 7 is raised and moved to a position over the first vessel $v_1$ of the group $G_1$ (steps $S_6, S_7$). Then, the support head 7 is lowered into the vessel $v_1$ (step $S_8$) for paraffin removal from specimens. At this time, the cage 3 supported by the support head 7 is shaked in xylene a few times while rotating the pulse motor 65 reversely whereby the specimen attached to the slide glass can contact xylene in a good condition (step $S_9$). After the shaking operation (reciprocal movement) of the cage 3, the cage 3 is released in the first vessel $v_1$ (step $S_{10}$). After this step $S_{10}$, the support head 7 waits for the completion of immersion of the cage at a position over the vessel $v_1$ (step $S_{x1}$). In all cases, after the completion of immersion of each cage 3 in the first vessel $v_1$ of the group $G_1$, the cage 3 is held by the support head 7 again to shake it and is moved into the second vessel $v_2$ (steps $S_{11}, S_{12}, S_{13}$). The cage 3 is shaked also in the second vessel $v_2$ when it is put thereinto and moved into the third vessel $v_3$ therefrom. After the support head 7 releases the cage 3 into the second vessel $v_2$, the support head 7 is moved to a position over a next vessel of the group $G_{10}$ to hold a next cage 3 therein and support it into the first vessel $v_1$ (step $S_{x2}$). Anyway, the cage 3 is transported into the third vessel $v_3$ containing the clearest xylene from the second vessel $v_2$ adjacent to the vessel $v_3$ while such a shaking operation is carried out (step $S_{14}$). Then the support head 7 transports the next cage 3 into the second vessel $v_2$ from the first vessel $v_1$ (step $S_{x3}$). After the cage 3 is immersed in the vessel $v_3$ for some time, the cage 3 is moved to the first vessel $v_1$ of the group $G_3$ to immerse it into alcohol and then moved to the vessels $v_2$ and $v_3$ of the same group $G_3$ (step $S_{15}$). After this, the cage 3 is moved to a vessel of the group $G_5$ and to a vessel of the group $G_6$ for washing it (step $S_{16}$). These steps are carried out before a dyeing step. Then, the cage 3 is moved into a predetermined vessel v containing a dyeing reagent corresponding to a dyeing method to be selected ($S_{17}$).

During the immersion of a cage in each vessel, the support head 7 holds other cages to transport them into other vessels (steps $S_{x4}$, $S_{x5}$). Each cage 3 is shaked when it is put into each vessel and it is removed from one vessel to another vessel.

After the specimen is dyed, the cage 3 is moved to the first vessel $v_1$ containing alcohol of the group $G_4$ for dehydration and then moved to the vessels $v_2$ and $v_3$ of the same group $G_4$ (step $S_{18}$). Thereafter, the cage 3 is moved to the first vessel $v_1$ containing xylene of the group $G_2$ for alcohol removal from the specimen (step $S_{19}$). Finally, the cage 3 is moved into a vessel v containing xylene of the group $G_{11}$ (step $S_{20}$). Between the steps $S_{17}$, $S_{18}$; $S_{18}$, $S_{19}$; and $S_{19}$, $S_{20}$, various operations are carried out by the support head 7 (steps $S_{x6}$, $S_{x7}$, $S_{x8}$). All cages are treated in this manner.

Furthermore, as the reagents of the groups $G_1$ to $G_4$ are used many times during dyeing operation, they are degraded in a short time. Accordingly, those reagents must be often exchanged for new ones. To facilitate this operation, the time for exchanging of those reagents may be programmed and the limit of the number of times may be predetermined. Further, a sensor for sensing degradation of a reagent may be provided.

Figure 13:
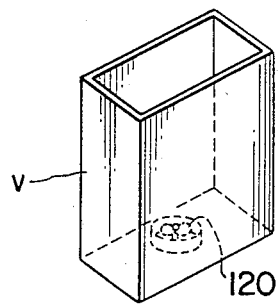
FIG. 13 is a perspective view of a vessel with a screw as a shaking mechanism.

During a dyeing operation, it is important to shake each cage in each vessel. Instead of shaking each cage, a screw 120 may be provided at a bottom of a vessel v for generating a liquid flow as shown in FIG. 13.

According to this invention, as when one cage is immersed in a vessel, the support head 7 can transport the other cage to another vessel, various dyeing operations can be carried out with respect to a plurality of cages.

What is claimed is:

1. An apparatus for dyeing specimens automatically preparatory to microscopic examination, comprising:
   (a) a casing having an open front side;
   (b) a main table and an upper table provided in said casing, said upper table being disposed above a front part of the main table at a position toward the front side of the casing thereby to provide an open front space between the two tables;
   (c) a plurality of vessels containing various reagents and arranged regularly on the main table longitudinally and laterally thereof in such a manner that the vessels can be taken out of the casing through said open front space;
   (d) a plurality of other vessels arranged on the upper table longitudinally thereof;
   (e) a plurality of specimen cages each having means for removably accommodating at least one piece of slide glass with a specimen thereon, and hanging means provided on a head portion;
   (f) means for transporting said specimen cages over said vessels longitudinally and laterally of said tables from one vessel to another, said transporting means having a support head with finger means automatically operable to be engaged with or disengaged from said transporting means also having means for moving said support head vertically to cause each specimen cage held thereby to move into and out of one of the vessels; and
   (g) a controller for controlling said transporting means to cause the same to move longitudinally, laterally and vertically and to cause said finger means to open and close for engagement with and disengagement from said hanging means, said controller controlling the transporting means according to a dyeing program in such a manner that the specimen cages are lowered into and raised out of the various reagents from one vessel to another and that one of the specimen cages is disengaged from said finger means, after being lowered into a reagent, and left therein while the support head is transporting another specimen cage from vessel to vessel, the one specimen cage left being thereafter raised out of said reagent by the support head which had returned to the vessel containing said reagent.

2. An apparatus according to claim 1, further comprising a plurality of proximity switches provided under the main and upper tables for sensing the existence of the vessels and display lamps provided on the front of the casing and connected to the proximity switches, respectively.

3. An apparatus according to claim 1, further comprising a cover provided on the front of the casing to openably close said open front space.

4. An apparatus according to claim 1, wherein said finger means are urged by a spring means in a direction to disengage said hanging means, and said support head has a drive means for moving the finger means in a direction to engage said hanging means against the force of the spring means.

5. An apparatus according to claim 1, further comprising means for shaking the specimen cage in up-and-down movement in the reagent of the vessel, said means for shaking being formed by said means for moving said support head vertically.

6. An apparatus according to claim 1, wherein the vessels on the main table are divided into groups some groups of which have liquid supply means for supplying a liquid thereinto from a tank accommodated in the casing.

7. An apparatus according to claim 6, further comprising trays each placed slidably on the main table and receiving thereon each one of said groups of the vessels.

8. An apparatus according to claim 7, further comprising a plurality of proximity switches provided under the main and upper tables for sensing the existence of the vessels and trays, and display lamps provided on the front of the casing and connected to the proximity switches, respectively.

* * * * *